(12) United States Patent
Hartley et al.

(10) Patent No.: US 9,603,696 B2
(45) Date of Patent: Mar. 28, 2017

(54) DEVICE FOR TREATING AORTIC DISSECTION

(75) Inventors: David Ernest Hartley, Subiaco (AU);
Erik E. Rasmussen, Slagelse (DK);
Thomas C. McIntyre, Beamaris (AU)

(73) Assignee: Cook Medical Technologies LLC, Bloomington, IN (US)

( * ) Notice: Subject to any disclaimer, the term of this patent is extended or adjusted under 35 U.S.C. 154(b) by 954 days.

(21) Appl. No.: 13/184,256

(22) Filed: Jul. 15, 2011

(65) Prior Publication Data

US 2011/0270377 A1 Nov. 3, 2011

Related U.S. Application Data

(62) Division of application No. 11/237,120, filed on Sep. 28, 2005, now Pat. No. 7,993,383.

(Continued)

(51) Int. Cl.
*A61F 2/07* (2013.01)
*A61F 2/90* (2013.01)
(Continued)

(52) U.S. Cl.
CPC .................. *A61F 2/07* (2013.01); *A61F 2/90* (2013.01); *A61F 2/95* (2013.01); *A61F 2/966* (2013.01);
(Continued)

(58) Field of Classification Search
CPC ...... A61F 2/07; A61F 2/89; A61F 2/90; A61F 2/95; A61F 2/966; A61F 2002/826;
(Continued)

(56) References Cited

U.S. PATENT DOCUMENTS 5,035,706 A   7/1991   Giantureo et al.
5,824,040 A   10/1998  Cox et al. .................... 623/1.35
(Continued)

FOREIGN PATENT DOCUMENTS

CA   2486390   12/2003
EP   1440673   7/2004
(Continued)

OTHER PUBLICATIONS

Examiner's First Report for corresponding AU Application No. 2005289395, dated May 18, 2010, 1 page.
(Continued)

*Primary Examiner* — Julian W Woo
*Assistant Examiner* — Lucas Paez
(74) *Attorney, Agent, or Firm* — Brinks Gilson & Lione

(57) ABSTRACT

A stent assembly (42) adapted for endoluminal placement by endovascular deployment for the treatment of a false lumen (10) associated with a vascular dissection. The stent assembly has a number of self expanding stents (35) connected together to define an elongate substantially cylindrical lumen wall engaging surface. The stents are adapted to provided pressure on the wall of the lumen adjacent to and extending away from a rupture. A deployment device (40) for the stent assembly includes a sheath (48) and a retention and release arrangement (50) to retain the proximal end (37) of the stent graft to the deployment device. Release of the stent assembly is by withdrawal of the sheath before release of its proximal end by the use of a trigger wire (54) of the retention and release arrangement.

11 Claims, 13 Drawing Sheets

Related U.S. Application Data

(60) Provisional application No. 60/613,950, filed on Sep. 28, 2004.

(51) Int. Cl.
*A61F 2/95* (2013.01)
*A61F 2/966* (2013.01)
*A61F 2/82* (2013.01)
*A61F 2/89* (2013.01)

(52) U.S. Cl.
CPC .......... *A61F 2/89* (2013.01); *A61F 2002/826* (2013.01); *A61F 2002/9505* (2013.01); *A61F 2002/9511* (2013.01); *A61F 2002/9665* (2013.01); *A61F 2220/0075* (2013.01); *A61F 2230/0067* (2013.01)

(58) Field of Classification Search
CPC ...... A61F 2002/9511; A61F 2002/9665; A61F 2002/9505; A61F 2230/0067; A61F 2220/0075; A61F 2/962; A61F 2/2427; A61F 2/2436; A61F 2/2439; A61F 2002/011; A61F 2002/016; A61F 2/2418; A61F 2/2466
USPC ....................... 623/1.11–1.18, 1.23
See application file for complete search history.

(56) References Cited

U.S. PATENT DOCUMENTS

| | | | |
|---|---|---|---|
| 5,824,058 A | 10/1998 | Ravenscroft et al. ....... 623/1.11 |
| 5,919,225 A * | 7/1999 | Lau et al. .................... 606/198 |
| 6,251,132 B1 | 6/2001 | Ravenscroft et al. |
| 6,641,606 B2 * | 11/2003 | Ouriel et al. ................ 623/1.12 |
| 6,743,219 B1 * | 6/2004 | Dwyer et al. ................ 604/525 |
| 6,878,159 B2 | 4/2005 | Iwasaka et al. |
| 7,335,224 B2 | 2/2008 | Ohienschaeger ........... 623/1.11 |
| 7,611,528 B2 | 11/2009 | Goodson et al. ........... 623/1.11 |
| 2001/0037142 A1 * | 11/2001 | Stelter et al. ............... 623/1.13 |
| 2002/0151953 A1 | 10/2002 | Chobotov et al. |
| 2003/0233140 A1 * | 12/2003 | Hartley et al. ............... 623/1.11 |
| 2004/0098079 A1 | 5/2004 | Hartley et al. |
| 2004/0176832 A1 * | 9/2004 | Hartley .................... A61F 2/07 623/1.11 |
| 2005/0049667 A1 | 3/2005 | Arbefeuille et al. ........ 623/1.11 |
| 2006/0259119 A1 | 11/2006 | Rucker ..................... 623/1.11 |
| 2006/0276872 A1 * | 12/2006 | Arbefeuille et al. ........ 623/1.11 |
| 2008/0140178 A1 | 6/2008 | Rasmussen et al. ......... 623/1.11 |
| 2008/0264102 A1 | 10/2008 | Berra ........................ 623/1.11 |

FOREIGN PATENT DOCUMENTS

| | | |
|---|---|---|
| JP | H 0581257 B2 | 11/1993 |
| JP | 2003-135604 | 5/2003 |
| JP | 2005-535364 A | 11/2005 |
| WO | WO 99/29262 A1 | 6/1999 |
| WO | WO 03/101518 A1 | 12/2003 |
| WO | WO 2004/049978 A1 | 6/2004 |

OTHER PUBLICATIONS

Examination Report for corresponding CA 2,581,857, dated Mar. 21, 2012, 2 pages.
PCT International Search Report and Written Opinion for corresponding PCT/US2005/034965 dated Feb. 15, 2006, 12 pages.
PCT International Preliminary Report on Patentability for corresponding PCT/US2005/034965 dated Feb. 12, 2007, 6 pages.
Japanese Office Action and English translation for corresponding JP 2007-534752, dated Nov. 28, 2008, 4 pages.
Japanese Final Decision for Rejection and English translation for corresponding JP 2007-534752, dated Sep. 16, 2009, 4 pages.
Japanese Appeals Questioning dated Nov. 11, 2010 and Office Action dated Feb. 26, 2010 and English translation for JP 2007-534752, 7 pages.

* cited by examiner

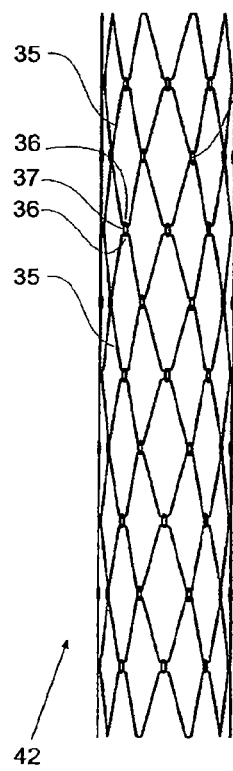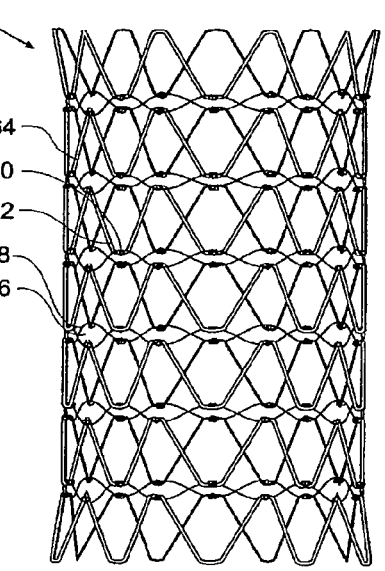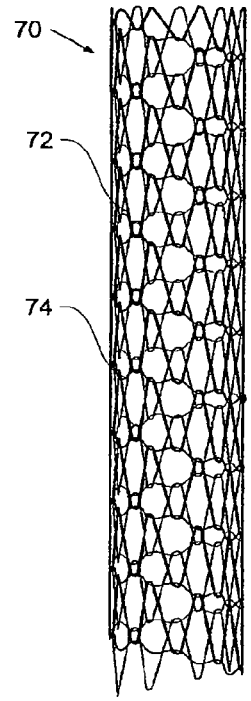
Fig 8
Fig 9
Fig 11
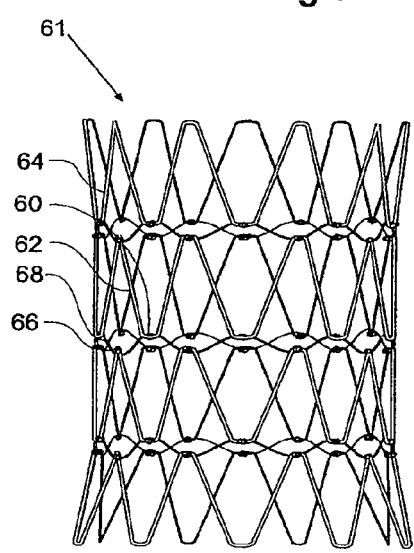
Fig 10

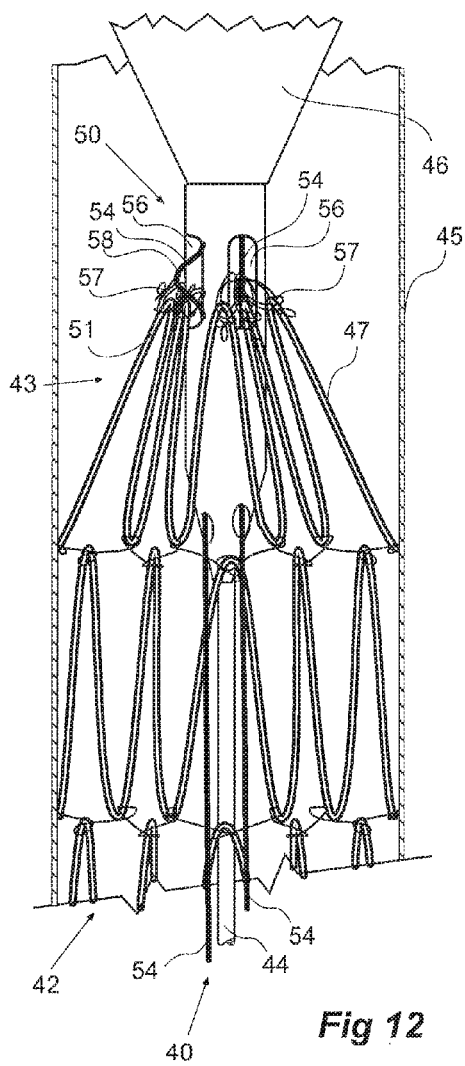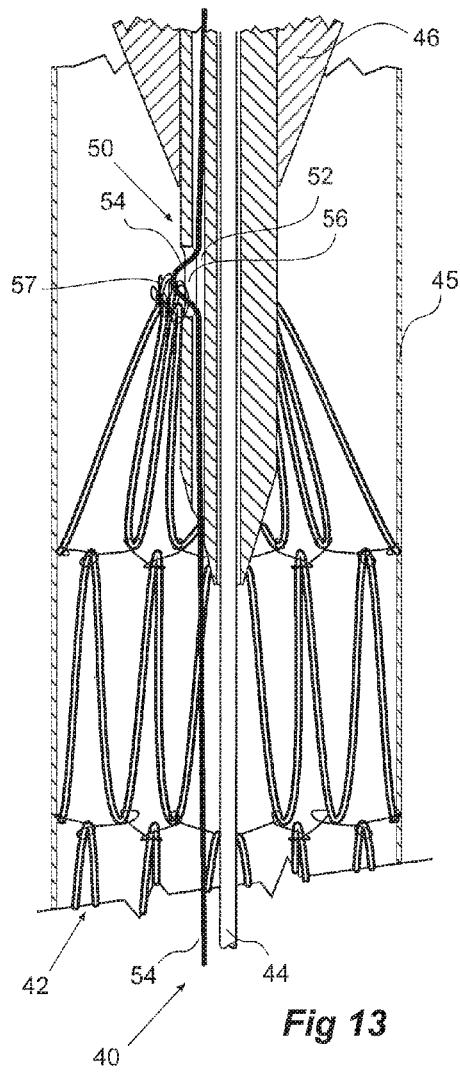

DEVICE FOR TREATING AORTIC DISSECTION

CROSS-REFERENCE TO RELATED APPLICATIONS

The present patent document is a divisional application that claims the benefit of priority under 35 U.S.C. §121 of U.S. patent application Ser. No. 11/237,120, filed Sep. 28, 2005, which claims priority to U.S. Provisional Patent Application Ser. No. 60/613,950, filed Sep. 28, 2004 which is hereby incorporated by reference in its entirety.

TECHNICAL FIELD

This invention relates to a device for the treatment of aortic arch disease and more particularly to the treatment of a form of aortic aneurysm known as an aortic dissection.

BACKGROUND OF THE INVENTION

An aortic dissection is a form of aneurysm to the descending aorta in which the wall of the aorta is damaged to such an extent that blood under pressure can get between inner and outer layers of the wall of the aorta to expand part of the wall into an inflated sac of blood which is referred to as a false lumen. The inflated sac of blood or false lumen so formed may extend some distance down the descending aorta and open out into the aorta again further down.

It is the object of this invention to provide a device and a method of treatment for an aortic dissection using the device will also be discussed.

Throughout this specification the term proximal with respect to both human or animal vasculature and the deployment device and prosthesis will be used to refer to the region closest to the heart or that part of the deployment device or of the prosthesis which when in use is closest to the heart and the term distal will be used for regions of the human or animal vasculature further from the heart and those parts of the deployment device or prosthesis which in use are further from the heart.

SUMMARY OF THE INVENTION

In one form the invention comprises a stent assembly comprising a plurality of self expanding zig zag stents and a link arrangement between adjacent stents so that the stents are linked together to define an elongate substantially cylindrical lumen wall engaging surface, each stent having a plurality of struts and bends between the struts and the link arrangement comprising a thread or fibre such as a suture thread which is knotted alternately to a bend of one stent and then a bend of an adjacent stent to provide a link thread of zig zag configuration, whereby upon endoluminal placement by endovascular deployment the stent assembly is adapted to provided pressure on the wall of the lumen to close off a false lumen in the lumen wall with each stent able to act independently of an adjacent stent. In an alternative form the invention comprises a stent assembly comprising a plurality of self expanding zig zag stents, links between adjacent stents so that the stents are linked together to define an elongate substantially cylindrical lumen wall engaging surface whereby upon endoluminal placement by endovascular deployment the stent assembly is adapted to provided pressure on the wall of the lumen to close off a false lumen in the lumen wall.

Preferably the links are flexible links. They can be provided by metal rings or can be a thread or fibre such as a braided suture thread knotted to or threaded around bends of the zig-zag stents. In the case of a braided suture material the material may be a 5.0 braided suture.

The stents can be formed from stainless steel or Nitinol.

The stent assembly can be in the form of a self expanding spiral stent of zig-zag configuration.

The stent assembly according to the present invention may provided in three lengths of 4, 6 or 8 stents long, nominally 88, 132 and 178 mm long and have a nominal maximum diameter of 46 mm.

In a preferred form the stents may be constructed from stainless steel wire having a diameter of 0.016 inches.

In a further form the invention comprises a deployment device and stent assembly for treatment of an aortic dissection, the stent assembly comprising at least one self expanding zig zag stent defining an elongate substantially cylindrical lumen wall engaging surface, and the deployment device comprising an elongate catheter adapted to be deployed over a guide wire, a nose cone at the proximal end of the elongate catheter, a trigger wire arrangement to retain a proximal end of the stent assembly just distal of the nose cone, a sheath over the elongate catheter adapted to retain the stent assembly in a contracted state around the elongate catheter, a release arrangement at the distal end of the elongate catheter to release the trigger wire arrangement and a grip mounted to the sheath to enable withdrawal of the sheath arrangement, whereby upon endoluminal placement by endovascular deployment, retraction of the grip and sheath and release of the stent assembly the stent assembly expands to provide pressure on the wall of the lumen to close off a false lumen in the lumen wall.

Preferably the stent assembly comprises a plurality of self expanding zig zag stents and a link arrangement between adjacent stents so that the stents are linked together to define an elongate substantially cylindrical lumen wall engaging surface, each stent having a plurality of struts and bends between the struts and the link arrangement comprising a biocompatible thread or fibre such as a suture thread and knots which are knotted alternately to a bend of one stent and then a bend of an adjacent stent to provide a link thread of zig zag configuration, whereby upon endoluminal placement by endovascular deployment the stent assembly is adapted to provided pressure on the wall of the lumen to close off a false lumen in the lumen wall with each stent able to act independently of an adjacent stent.

Preferably the distal end of the stent assembly is retained to the deployment device by a distal trigger wire arrangement and there are means at the distal end of the elongate catheter to release the distal trigger wire arrangement.

Preferably the trigger wire arrangement comprises at least one trigger wire extending from the release mechanism through the deployment catheter and the trigger wire engaged with the proximal end of the stent assembly.

There can be three trigger wires extending from the release mechanism through the deployment catheter and each of the trigger wires engaging with a proportion of the bends of the proximal most stent of the stent assembly.

The engagement of the trigger wire with the proximal end of the stent assembly can comprise loops of a biocompatible thread engaging between bends of the proximal stent of the stent assembly and the trigger wire.

The proximal end of the stent assembly can comprise a proximal stent and a circumferential biocompatible thread including portions between adjacent bends of the proximal end of the proximal stent and the engagement of the trigger wire with the stent assembly comprises the thread portions between adjacent bends extending around the trigger wire. The elongate catheter can include means to supply an angiographic contrast medium at a distal end thereof through the catheter.

Links between adjacent stents of the stent assembly can be provided by a thread or fibre such as a suture thread which is knotted alternately to a bend of one stent and then a bend of an adjacent stent to provide a link thread of zig zag configuration.

In a further form the invention comprises a method of treatment of a false lumen of an aortic dissection comprising the steps of a) loading a stent assembly onto a deployment device, the stent assembly comprising a plurality of self expanding stents linked together and defining an elongate substantially cylindrical lumen wall engaging surface, the deployment device including a retention arrangement to retain the proximal end of the stent assembly in a retracted state and a trigger wire arrangement to release the retention arrangement to thereby release the proximal end of the stent assembly, a sheath to retain the entire the stent assembly in a retracted state and means to withdraw the sheath, b) endovascularly deploying the deployment device with the stent assembly loaded thereon to the site of the false lumen, c) withdrawing the sheath to expose the stent assembly such that it provides pressure against the wall of the lumen, d) releasing the proximal end of the prosthesis by means of releasing the trigger wire arrangement, and e) withdrawing the deployment device.

Preferably the distal end of the stent assembly is retained to the deployment device and previous or subsequent to the step of releasing the proximal end of the prosthesis the distal end is released.

In a further form the invention comprises a method of treatment of aortic dissection disease comprising a two stage process to close off a rupture associated with the aortic dissection and to apply pressure to a false lumen associated with the aortic dissection, the method comprising the steps of:

a) endovascularly deploying a first deployment device with a stent graft retained thereon to the site of the aortic dissection, b) checking by radiographic techniques that the stent graft is positioned over the site of the rupture, c) deploying the stent graft from the first deployment device, d) withdrawing the first deployment device, e) endovascularly deploying a second deployment device with a stent assembly loaded thereon to the site of the false lumen, the stent assembly comprising a plurality of self expanding stents linked together and defining an elongate substantially cylindrical lumen wall engaging surface, the deployment device including a retention arrangement to retain the proximal end of the stent assembly in a retracted state and a trigger wire arrangement to release the retention arrangement to thereby release the proximal end of the stent assembly, a sheath to retain the entire stent assembly in a retracted state and means to withdraw the sheath, f) withdrawing the sheath to expose the stent assembly such that it provides pressure against the wall of the lumen, g) releasing the proximal end of the prosthesis by means of releasing the trigger wire arrangement, and h) withdrawing the second deployment device.

Preferably the distal end of the stent assembly is also retained to the deployment device and previous or subsequent to the step of releasing the proximal end of the prosthesis the distal end is released.

BRIEF DESCRIPTION OF THE DRAWING

This then generally describes the invention but to assist with understanding reference will now be made to the drawings which show preferred embodiments of the invention.

In the drawings:

FIG. 8 shows a stent assembly according to one embodiment of this invention;

FIG. 9 shows an alternative embodiment of a stent assembly according to the invention;

FIG. 10 shows a still further embodiment of a stent assembly according to the invention;

FIG. 11 shows a still further embodiment of a stent assembly according to the invention;

FIG. 12 shows a detailed view of the proximal end of a deployment device with a stent assembly mounted thereon according to one embodiment the invention;

FIG. 13 shows a detailed cross sectional view of the proximal end of the deployment device and stent assembly of FIG. 12;

DETAILED DESCRIPTION

Figure 1:
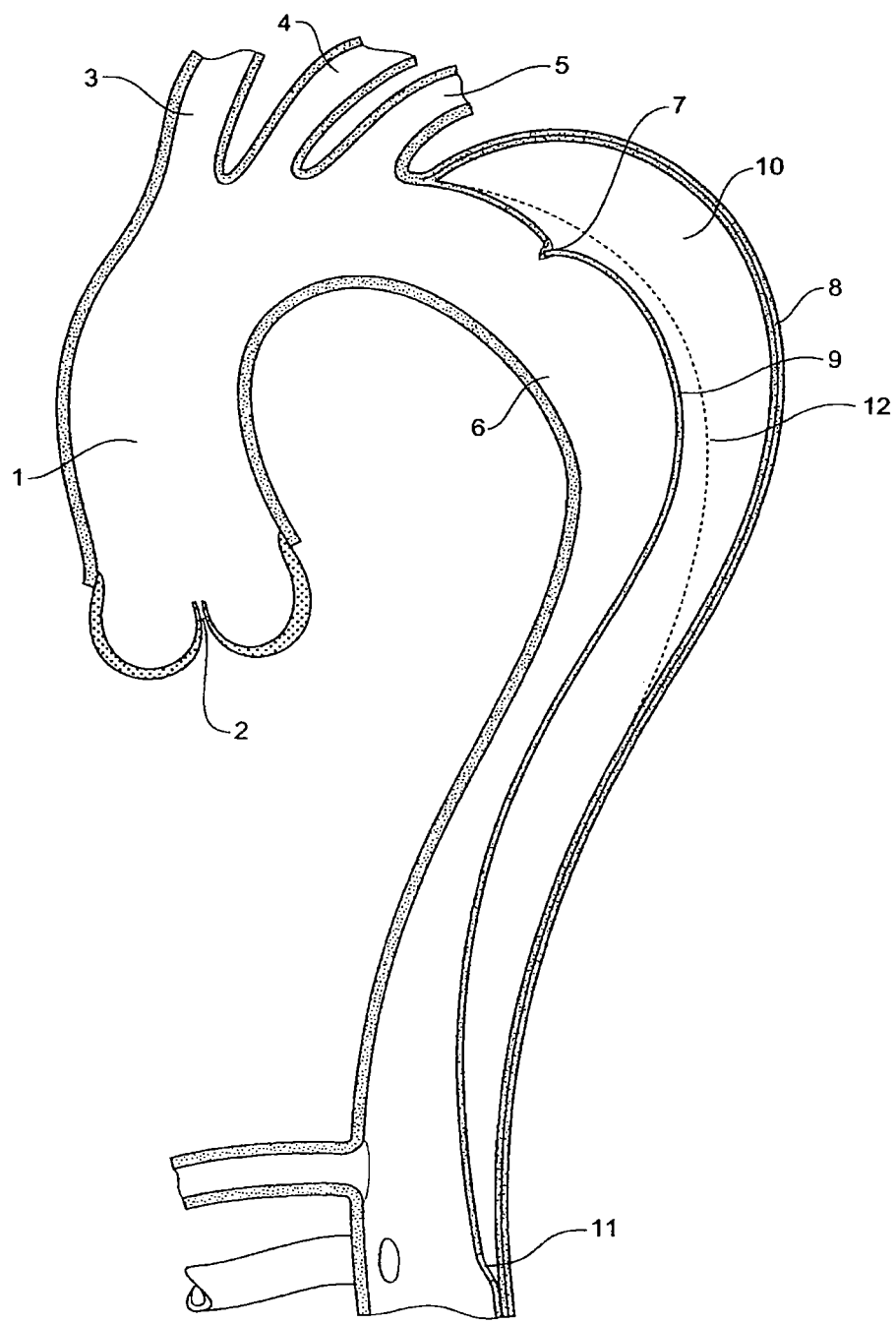
FIG. 1 shows a schematic view of an aorta with an aortic dissection.

Looking more closely to the drawings and in particular FIG. 1 it will be seen that the aorta comprises an ascending aorta 1 which receives blood from the heart though an aortic valve 2. At the upper end of the ascending aorta there are branches for the innominate artery 3 the left common carotid artery 4 and the subclavian artery 5. The aorta after these is referred to as the descending aorta 6 and it is in this region that an aortic dissection can occur. In an aortic dissection the wall of the descending aorta can be injured such as by a traumatic injury so that a partial rupture or tear 7 occurs and the wall of the descending aorta splits so that there is an outer wall 8 and an inner wall 9 between which a false lumen 10 occurs. At some distance down the false lumen 10 the false lumen may again open out into the aorta 6 such as at 11. The dotted line 12 shows the normal position of the wall of the aorta.

Treatment of the aortic dissection requires that the rupture 7 be closed off and the false lumen 10 deflated.

Figure 2:
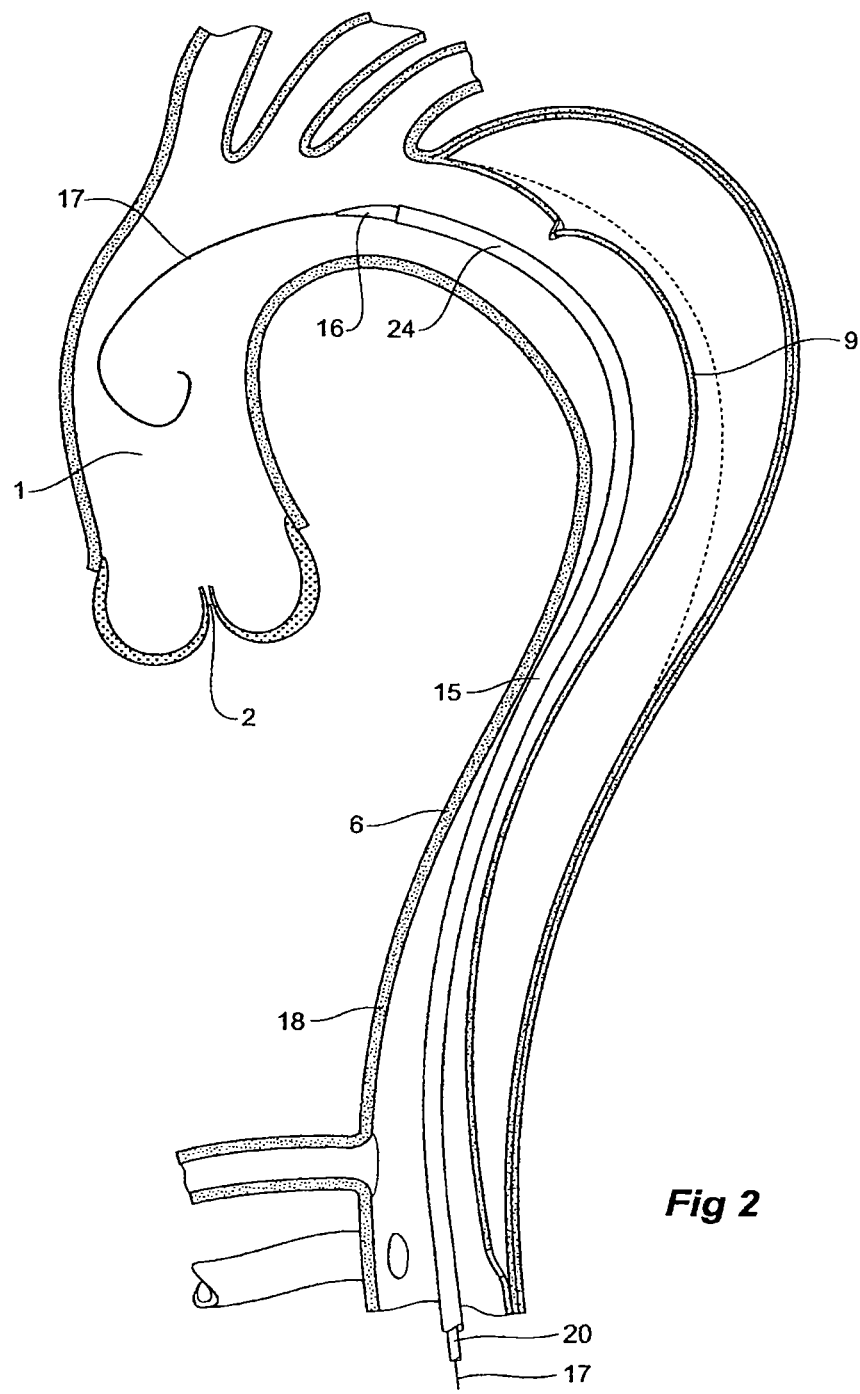
FIG. 2 shows the aorta shown in FIG. 1 with a first deployment device inserted therein.

As can be seen in FIG. 2, a first deployment device 15 with a nose cone 16 has been advanced over a guide wire 17 through the true lumen 18 of the descending aorta 6. Preferably the deployment device is inserted through a femoral artery and up through the iliac arteries into the aorta using a technique known as the Seldinger technique.

Once the deployment device is in substantially the correct place angiographic fluids may be supplied through a hollow elongate catheter 20 in the deployment device to exit through the nose cone 16 so that with the use of angiographic contrast medium the region can be visualised by radiographic techniques.

Figure 3:
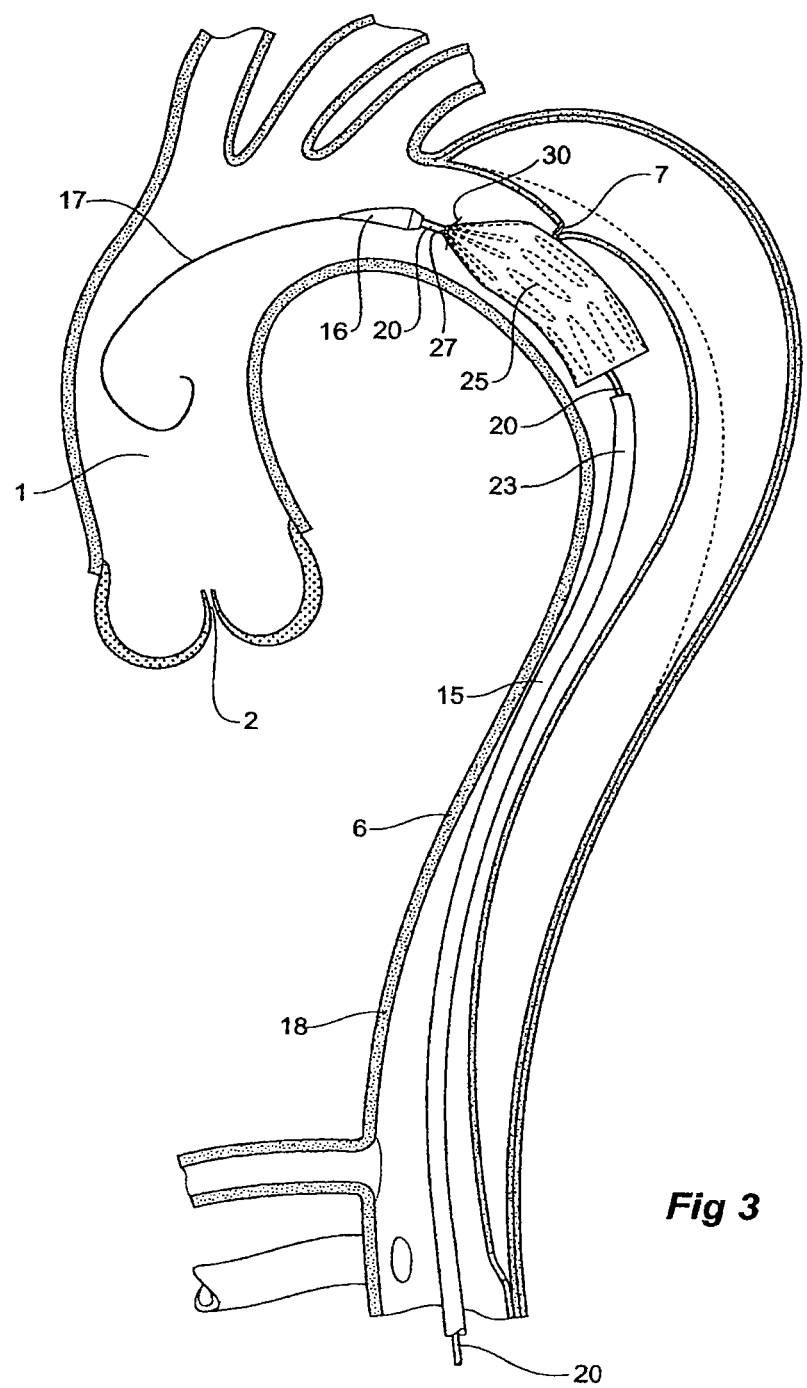
FIG. 3 shows the first stage of deployment of a covered stent graft prosthesis.

When the deployment device is found to be in the correct position, the sheath 24 of the deployment device is withdrawn to the position as shown in FIG. 3 at which stage the stent graft 25 is expanded except that the proximal end 27 is retained by a trigger wire retention mechanism to the central catheter 20. At this stage the pressure of blood flow from the heart will still tend to cause blood flow around the stent graft 25.

Figure 4:
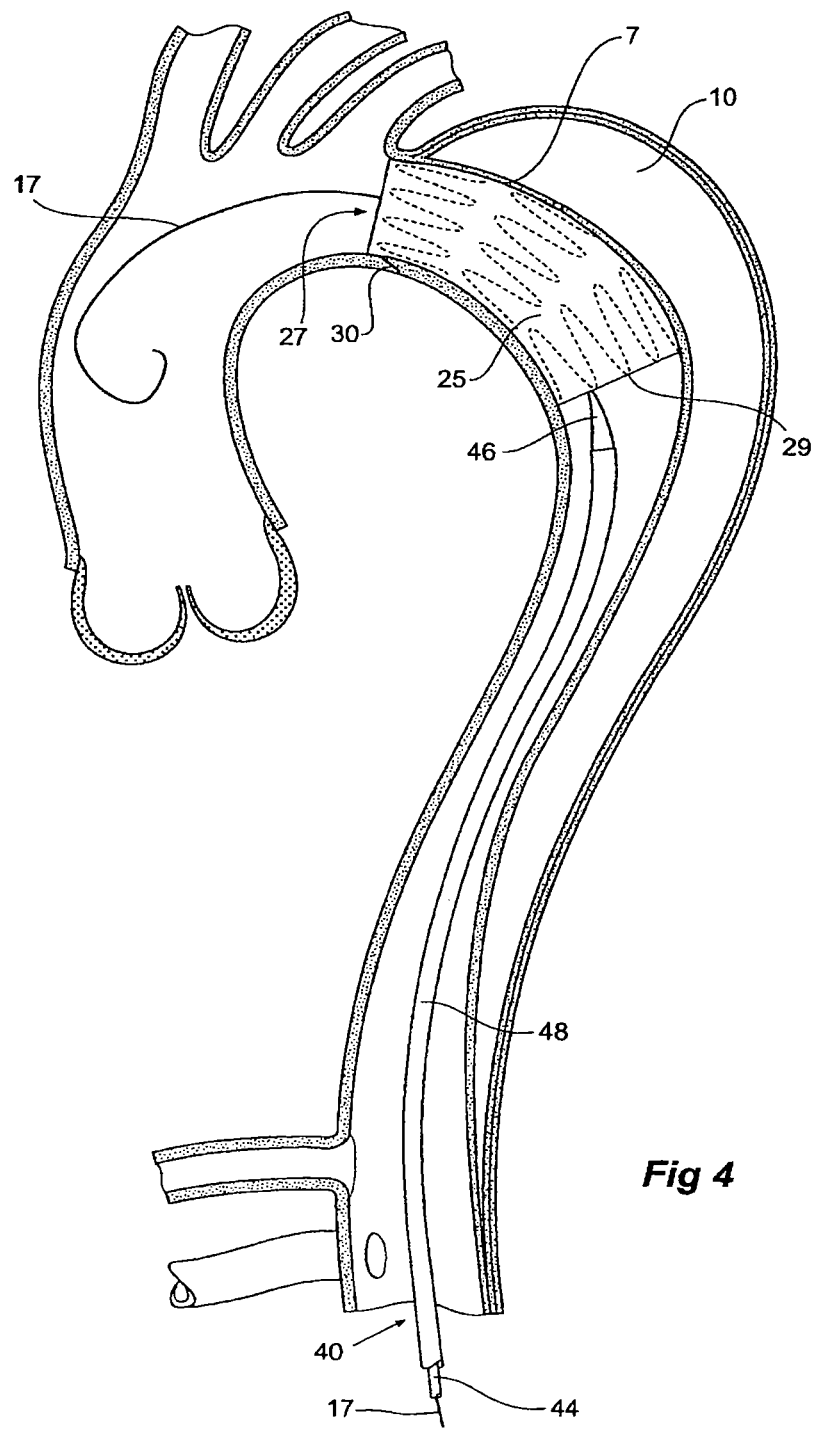
FIG. 4 shows the fully deployed covered stent graft prosthesis and the deployment of a second deployment device.

Next a trigger wire release mechanism is released so that the proximal end 27 of the prosthesis 25 is allowed to open as shown in FIG. 4 and the barbs 30 on the proximal end of 27 of the stent graft 25 engage against the wall of the aorta to securely fix the stent graft 25 in the upper end of the descending aorta with the stent graft 25 covering the rupture 7 and essentially closing it off so that blood can no longer flow into the false lumen 10. Blood can then flow through the stent graft and exit out at the distal end 29 of the stent graft 25.

Next, the first deployment device can be withdrawn and a second deployment device 40 deployed over the guide wire 17. Alternatively the first deployment device 15 can be withdrawn leaving the sheath 24 and guide wire 17 in place and a second deployment device 40 can be deployed through the sheath 24 and over the guide wire 17.

The second deployment device 40 has a elongate deployment catheter 44 and a nose cone 46 and carries a stent assembly 42 as will be discussed in relation to FIGS. 8 to 11 and the stent assembly 42 is mounted onto the second deployment device 40 by various arrangements as will be discussed in relation to FIGS. 12 to 17.

Figure 5:
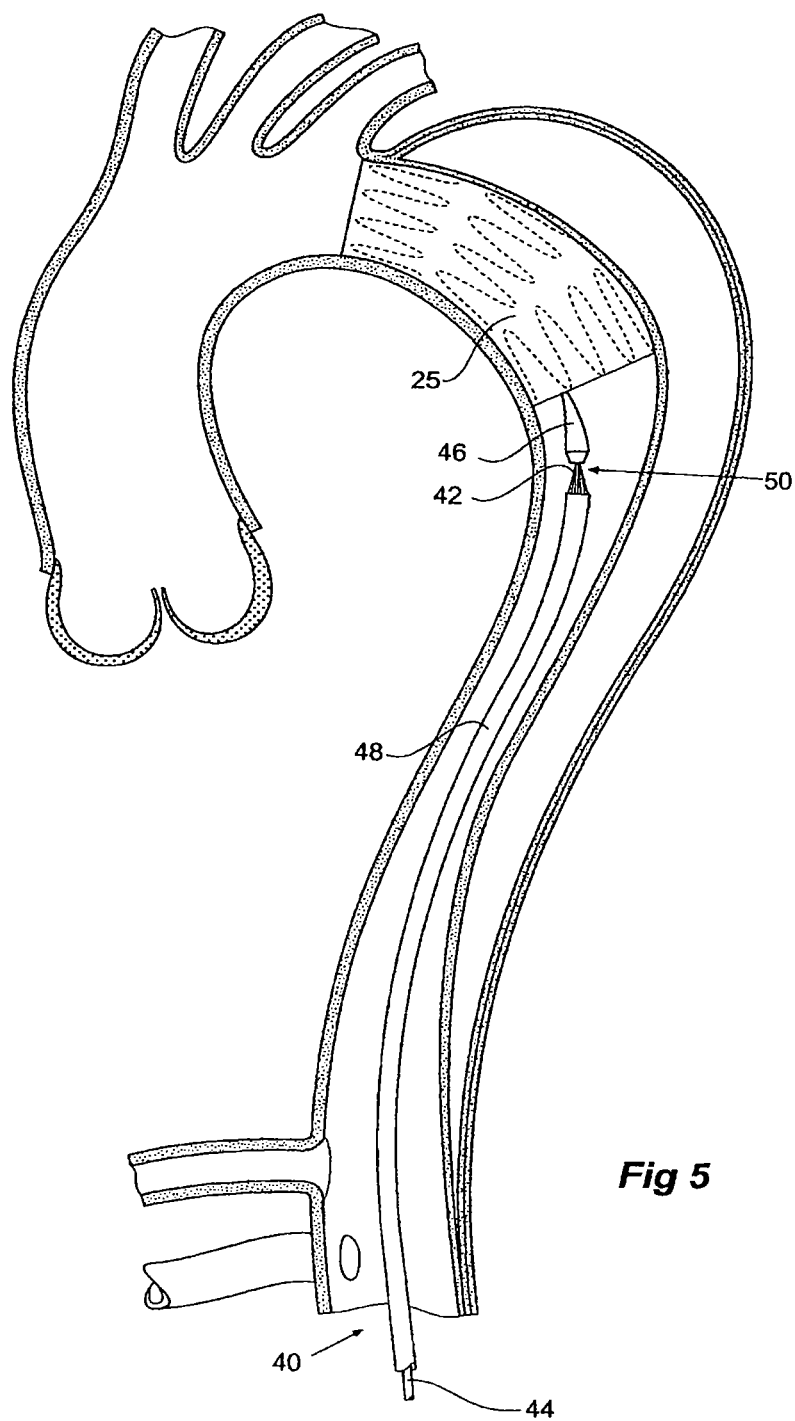
FIG. 5 shows the first stage of the deployment of a stent assembly from the second deployment device.
Figure 6:
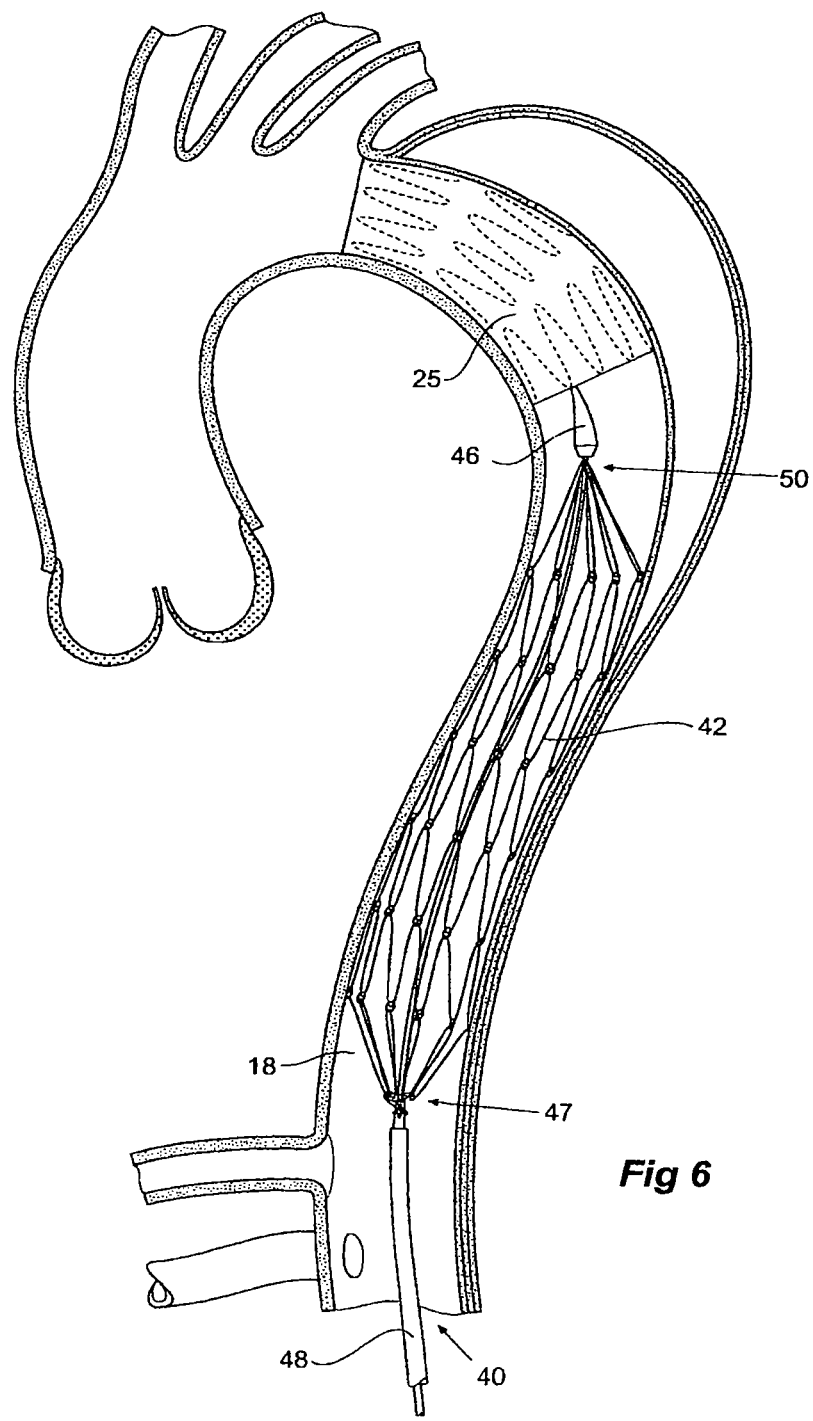
FIG. 6 shows the next stage of the deployment of the stent assembly from the second deployment device.

When the second deployment device is in place as shown in FIG. 4 the sheath 48 of the second deployment device 40 is withdrawn as shown in FIGS. 5 and 6 so that the stent assembly 42 is exposed and gradually released until it is fully released except where it is retained by a release mechanism 50 just distal of the nose cone 46 as will be discussed in relation to FIGS. 12 to 17. There is optionally also a distal retention arrangement 47 at the distal end of the stent assembly. The distal retention arrangement 47 can be released either before or after release of the proximal retention arrangement 50. The self expanding stents of the stent assembly 42 are allowed to engage against the wall of the true lumen 18 and provide pressure onto the wall particularly where the false lumen occurs to gradually deflate and close off the false lumen as shown in FIG. 6.

If the stent assembly 42 was not retained at its proximal end just distal of the nose cone 46 then there is a danger that, as the sheath 48 was withdrawn or the stent assembly pushed out of the sheath 48, its proximal end could fan out and actually turn inside out or at least jamb in an unacceptable position in the descending aorta. This could put unacceptable pressure on the wall of the aorta which could be torn or ruptured.

The distal retention arrangement 47 is particularly useful to prevent a too rapid release of the distal end of the stent assembly.

Figure 7:
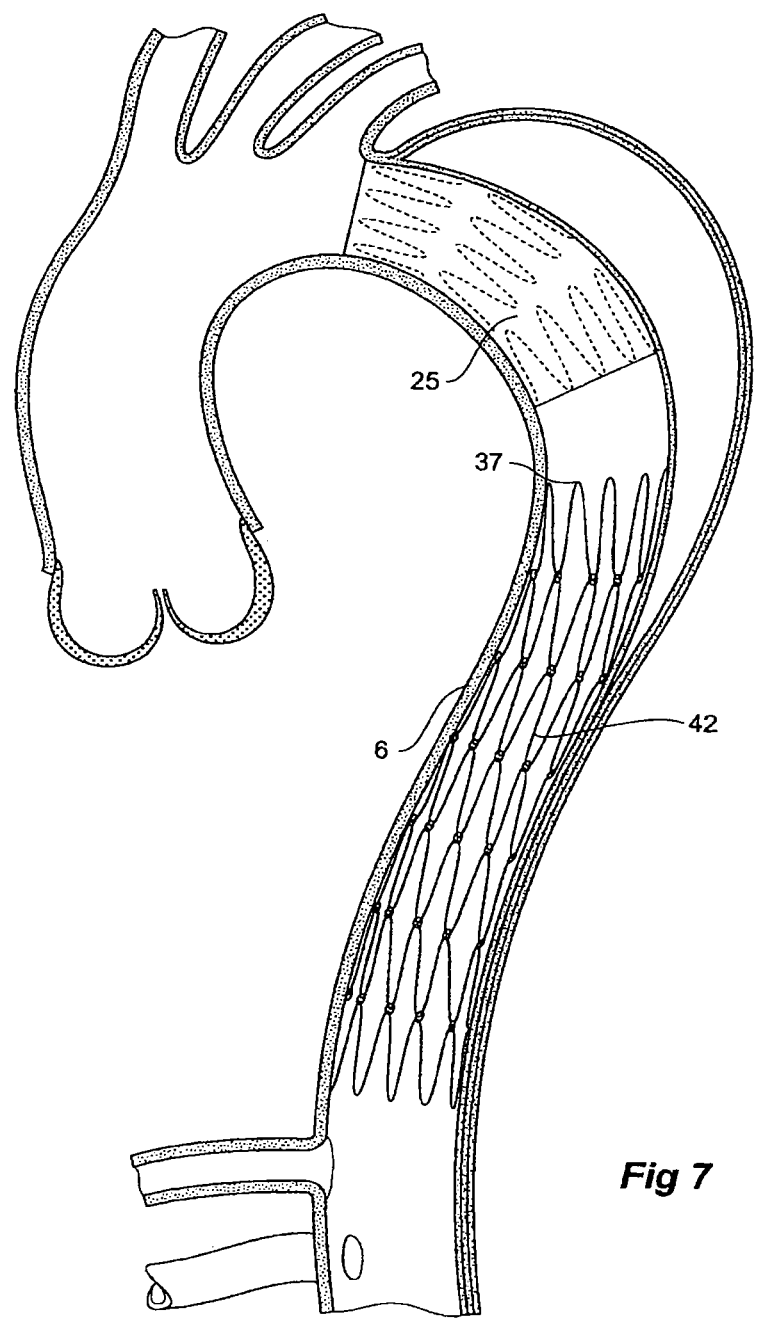
FIG. 7 shows the fully deployed stent assembly.

The release mechanism 50 can then be released and then the entire second deployment device can be withdrawn to leave the stent assembly 42 in place in the descending aorta 6 as shown in FIG. 7.

FIG. 7 shows the stent assembly 42 placed distally of the covered stent graft 25 but in an alternative arrangement the stent assembly 42 could be placed so that its proximal end 37 is within the distal end of the stent graft 25.

FIG. 8 shows a first embodiment of a stent assembly 42 for use with the method of the present invention. The stent assembly 42 has a plurality of zig zag self expanding Gianturco type zig zag stents 35 and each apex 36 of the stents is linked to the next stent up or down by flexible links 37. The flexible links may be wire rings or loops of thread or fibre such as a suture thread. The flexible links enable each stent of the stent assembly to expand separately as the false lumen is deflated which may occur over a period of several days or weeks. The stents provide gradual pressure on the wall of the lumen to close the false lumen and open up the true lumen. It will be realised that different numbers of stents may be used depending upon the nature of the aortic dissection and the length of aorta to be opened and the dimensions of the rupture in the wall of the aorta.

FIGS. 9 and 10 show further embodiments of stent assemblies 59 and 61 respectively according to the present invention. In these embodiments bends 60 between the struts 62 of the zig zag self expanding stents 64 are linked by means of a fibre or thread 68 such as a suture thread with the thread knotted to each bend 60 by a knot 66 so that each self expanding stent can act independently of its neighbours. It will be noted that the thread or fibre is knotted alternately to a bend of one stent and then a bend of an adjacent stent to provide a link thread of zig zag configuration. The stent assembly 59 in FIG. 9 can have up to eight stents with a total length of from 178 mm and a diameter when expanded of 46 mm. The stent assembly 61 in FIG. 10 has four stents with a total length of 88 mm and a diameter when expanded of 46 mm. A further embodiment may have a length of 132 mm with six stents. In one embodiment the stents may be formed from 0.016 inch diameter stainless steel wire but in other embodiments there may be differing wire thicknesses to vary the radial force applied to the vessel wall.

FIG. 11 shows a still further embodiment of the stent assembly of the invention. In this embodiment the stent assembly 70 is formed from a continuous spiral of zig-zag stent 72 with again loops in adjacent spirals joined by a thread 74 such as a suture thread. Again suitable knots may be used to assist with the controlled linking of adjacent portions of the spiral stent.

In an alternative embodiment of the invention of a stent assembly according to the invention the stents and the links between the stents may be in the form of a mesh and formed from a biocompatible and biodegradable mesh material so that after it has performed its work of providing a radial pressure onto the wall of the aorta it can biodegrade in the bloodstream.

FIG. 12 shows a detailed view of the proximal end of a deployment device with a stent assembly mounted thereon according to one embodiment of the invention and FIG. 13 shows a detailed cross sectional view of the embodiment shown in FIG. 12.

The deployment device 40 has a deployment catheter 44 extending to a nose cone 46 at its proximal end. Just distal of the nose cone 46 a mounting and release mechanism 50 is provided to retain the proximal end 43 of the stent assembly 42. The stent assembly 42 is held in a contracted condition by a sheath 45. The mounting and release mechanism 50 has a catheter 53 around the deployment catheter 44 with at least one internal lumen 52 through which passes a trigger wire 54. An aperture 56 opening into the lumen 52 allows a bight 58 of the trigger wire to be exposed. Lengths of thread 57 such as a suture thread are used to fasten each of the apices 51 of the proximal-most stent 47 of the stent assembly 42 separately to the bight 58 of the trigger wire 54. When the stent assembly is to be finally released the trigger wire 54 is withdrawn and each of the threads 57 are released from the bight 58 so that the proximal end of the stent assembly can open against the vessel wall as discussed with reference to FIG. 6. The loops or lengths of thread 57 remain fastened to the apices of the proximal-most stent of the stent assembly.

Figure 14:
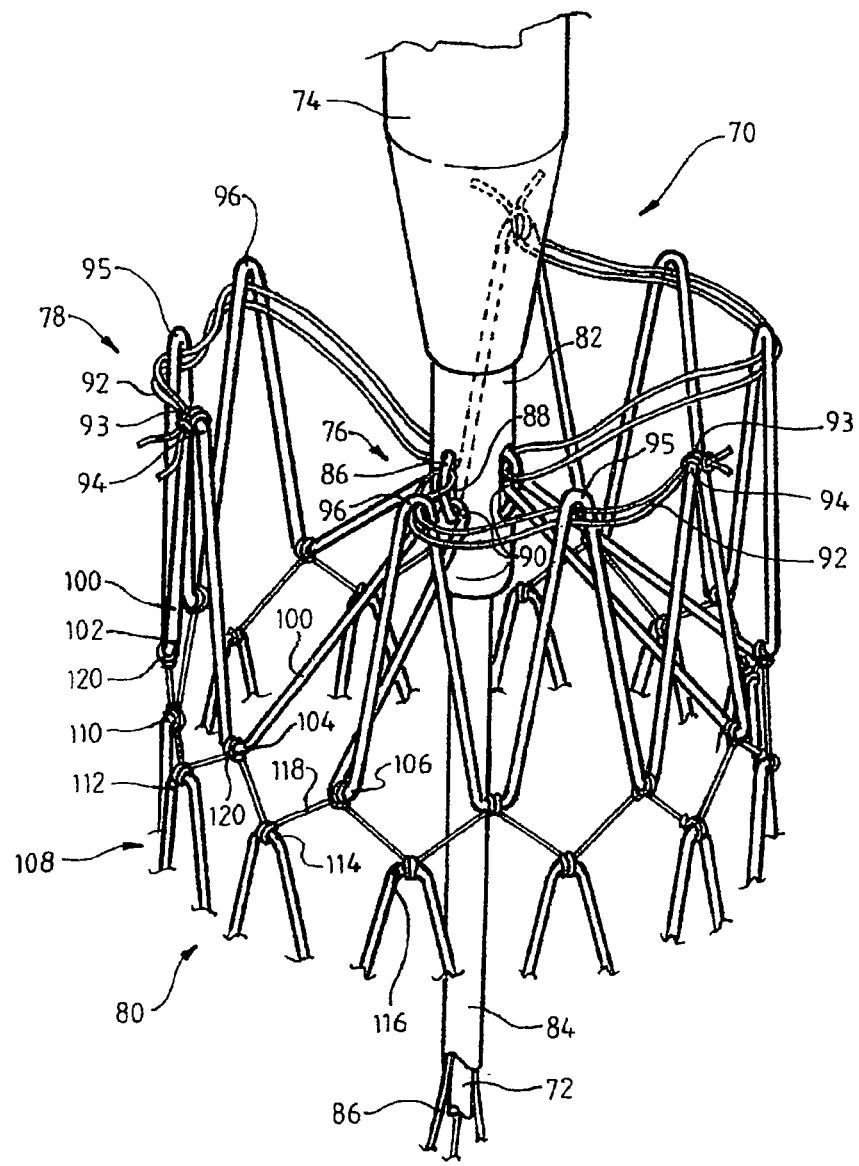
FIG. 14 shows a detailed view of part of the proximal end of a deployment device and an alternative method by which a stent assembly may be retained onto the deployment device according to one embodiment of the invention.
Figure 15:
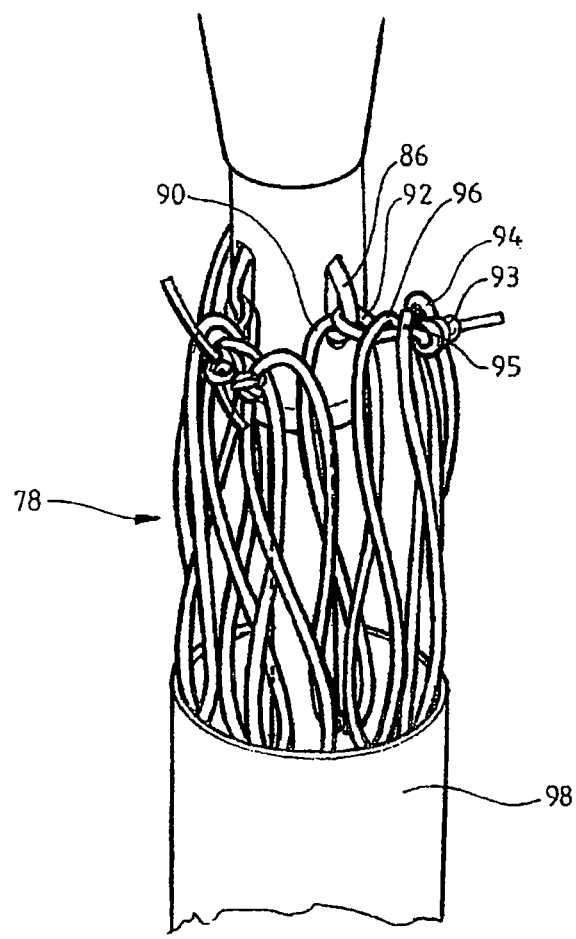
FIG. 15 shows the embodiment of FIG. 14 when retention sutures are pulled tight.

FIGS. 14 and 15 show a detailed view of part of the proximal end of a deployment device and an alternative method by which a stent assembly may be retained onto the deployment device. FIG. 15 shows the embodiment of FIG. 14 when the retaining sutures are pulled tight.

In FIG. 14 the deployment device 70 has a deployment catheter 72 extending to a nose cone 74 at its proximal end. Just distal of the nose cone 74 a mounting and release mechanism 76 is provided to retain the proximal stent 78 of the stent assembly 80. The mounting and release mechanism 76 comprises an enlarged end 82 of a trigger wire sleeve 84 and three trigger wires 86 which loop out of apertures 88 in the enlarged end 82 of a trigger wire sleeve 84.

One process for the loading of the proximal-most stent 78 of the stent assembly 80 to the deployment device 70 is as follows. In this embodiment the proximal stent 78 of the stent assembly 80 has twelve points or proximal bends.

In a first stage three equally spaced points 90 are mounted to respective trigger wires 86 by passing the respective trigger wire through the point or bend and then pushing the trigger wire back into the aperture 88. This holds these three points to the enlarged end 82 of the trigger wire sleeve 84. A portion of suture thread 92 is then tied with a knot 93 to the next point 94 clockwise from each of the points 90 captured by a trigger wire 86 (clockwise looking from the top—i.e. the proximal end). The suture thread 92 is then threaded clockwise through the next two points 95, 96 passing them from the outside inwards. The suture thread 92 is then passed beneath the respective trigger wire 86 and then re-threaded through the points 95, 96 in the same alignment as the initial threading. Then suture thread 92 is then tied to the loose end of the suture thread at the knot 93 at the point 94 and the suture thread is pulled tight and knotted three times. Then loose tails of suture thread are then cut short. When threaded this way, the stent points "stack up" neatly as the suture is tightened and the suture loops are short. If they are threaded in the opposite direction, they do not stack neatly, and the suture loops are longer.

FIG. 15 shows the suture threads 92 pulled tight and the points 94, 95 and 96 neatly stacked. The sheath 98 of the deployment device has been moved up to cover most of the stent assembly leaving only part of the proximal stent 78 exposed.

By the arrangement shown in FIGS. 14 and 15 upon release of the stent assembly the sutures will remain fixed to the points 94 and not cause problem within the blood vessel.

Other suturing methods may be devised in which the suture remains with the delivery device.

FIG. 14 also shows one method by which the adjacent stents of the stent assembly can be joined for optimal deployment. The proximal stent 78 of the stent assembly 80 has a plurality of struts 100 and bends 102, 104 and 106, for instance, between the struts 100 and the distally adjacent stent 108 has bends 110, 112, 114, and 116, for instance. The link arrangement between the stent 78 and the stent 108 comprises a thread or fibre such as a suture thread 118 which is knotted such as at 120 alternately to a bend 102 of one stent and then a bend 112 of an adjacent stent to provide a link thread of zig zag configuration. Upon endoluminal placement by endovascular deployment the stent assembly 80 is adapted to provided pressure on the wall of the lumen to close off a false lumen in the lumen wall with each stent able to act independently of an adjacent stent.

Figure 16:
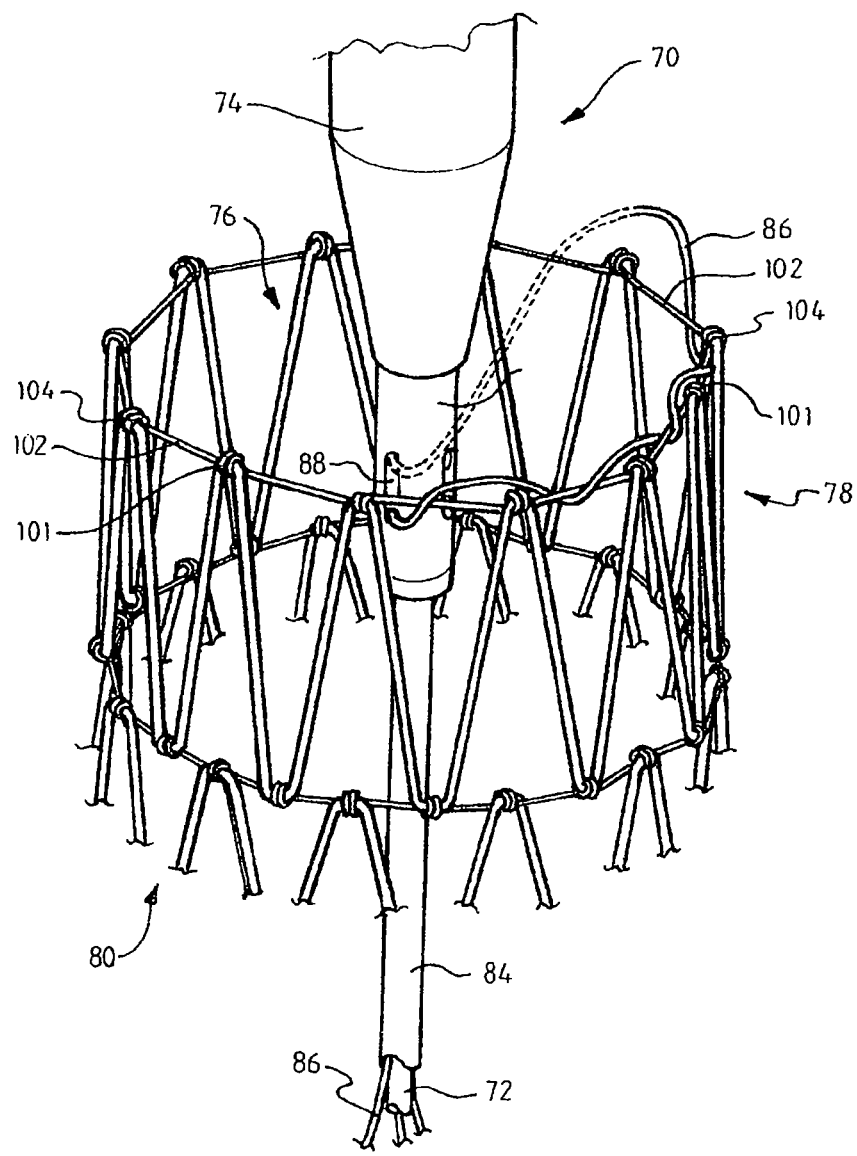
FIG. 16 shows a detailed view of part of the proximal end of a deployment device and an alternative method by which of a stent assembly may be retained onto the deployment device according to the invention.
Figure 17:
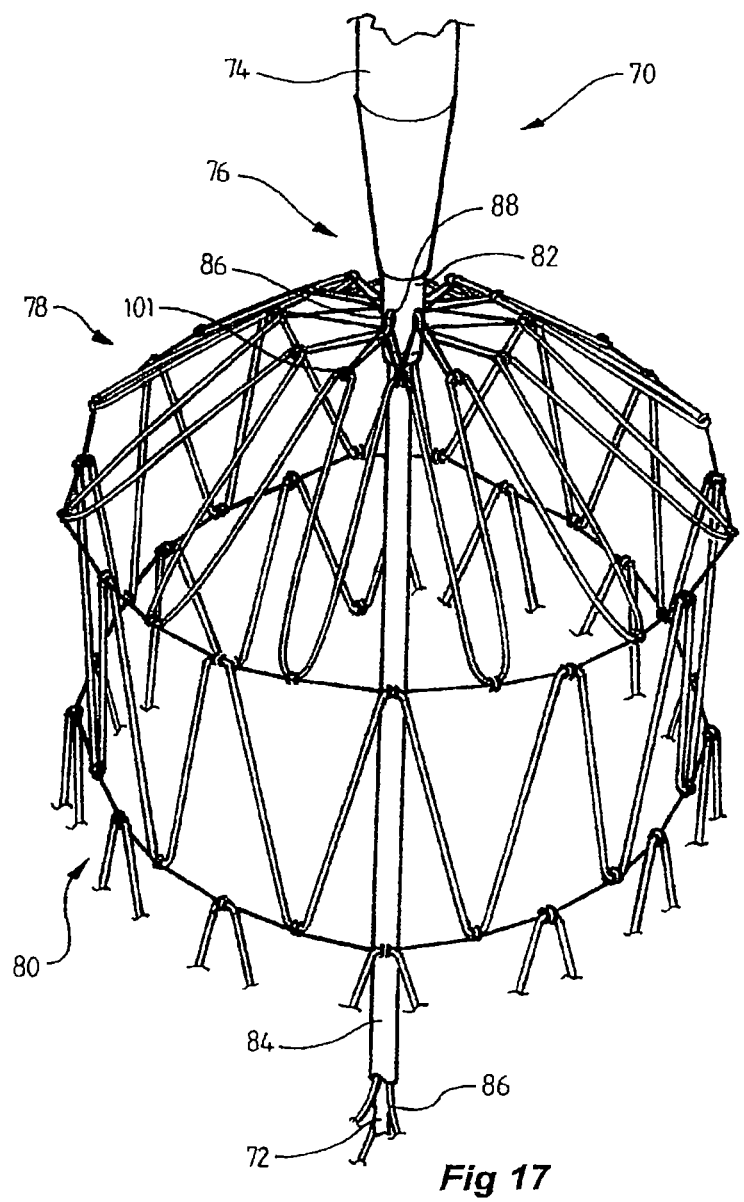
FIG. 17 shows the embodiment of FIG. 16 when the trigger wires are pulled into place.

FIGS. 16 and 17 show a detailed view of part of the proximal end of a deployment device and an alternative method by which a stent assembly may be retained onto the deployment device before and during delivery. FIG. 17 shows the embodiment of FIG. 16 when the proximal trigger wires are pulled into place.

In FIG. 16 the deployment device 70 has a deployment catheter 72 extending to a nose cone 74 at its proximal end. Just distal of the nose cone 74 a mounting and release mechanism 76 is provided to retain the proximal stent 78 of the stent assembly 80. The mounting and release mechanism 76 comprises an enlarged end 82 of a trigger wire sleeve 84 and trigger wires 86 which loop out of apertures 88 in the enlarged end 82 of a trigger wire sleeve 84.

The process for the loading proximal stent 78 of the stent assembly 80 onto the deployment device 70 according to this embodiment of the invention is a follows. In this embodiment the proximal stent 78 of the stent assembly 80 has twelve points or proximal bends 101.

For this embodiment the proximal end bends 101 of the proximal stent 78 are joined by a circumferential length of suture thread 102 and knotted 104 to each bend 101 in a similar manner to the joining of adjacent stents lower down the stent assembly 80.

To connect the trigger wire 86 to the proximal stent 78 the trigger wire is extended from the aperture 88 and then passed once around the suture 102 between each bend 101 for four portions between bends. This procedure is shown in FIG. 16. The end of the trigger wire is then placed back into the aperture 88, extended into the nose cone and pulled tight. This draws the lengths of suture material 102 between each bend 101 up to the aperture 88 to give the configuration shown in FIG. 17. This operation is repeated for the two other trigger wires 86.

By the arrangement shown in FIGS. 16 and 17 upon release of the stent assembly the suture thread 102 will remain fixed to the bends 101 and not cause problem within the blood vessel.

Throughout this specification various indications have been given as to the scope of the invention but the invention is not limited to any one of these but may reside in two or more of these combined together. The examples are given for illustration only and not for limitation.

What is claimed is:

1. A deployment device and stent assembly for treatment of a body vessel, the stent assembly comprising at least one self expanding zig zag stent having a plurality of proximal apices and defining an elongate substantially cylindrical lumen wall engaging surface, and the deployment device comprising an elongate catheter adapted to be deployed over a guide wire, a nose cone at a proximal end of the elongate catheter, a mounting and release mechanism to retain a proximal end of the stent assembly just distal of the nose cone, a sheath over the elongate catheter adapted to retain the stent assembly in a contracted state around the elongate catheter, a release arrangement at a distal end of the elongate catheter to release the mounting and release mechanism, and a grip mounted to the sheath to enable withdrawal of the sheath arrangement, whereby upon endoluminal placement by endovascular deployment, retraction of the grip and sheath and release of the stent assembly, the stent assembly expands to engage the body vessel, wherein the mounting and release mechanism comprises a trigger wire sleeve disposed over the elongate catheter, the trigger wire sleeve having a lumen, a proximal end, a plurality of apertures in a sidewall of the proximal end, a plurality of trigger wires extending through the lumen and looping out of the apertures, at least one length of filament joining proximal apices and knotted to the proximal apices to form a length of filament between adjacent apices, wherein the at least one length of filament forms a plurality of engagement loops, each of which engages one of the plurality of trigger wires and pulls the plurality of proximal apices toward the elongate catheter.

2. A deployment device and stent assembly as in claim 1 wherein the stent assembly comprises a plurality of self expanding zig zag stents each having proximal and distal apices with links between adjacent stents so that the stents are linked together to define the elongate substantially cylindrical lumen wall engaging surface.

3. A deployment device and stent assembly as in claim 2 wherein the links comprise at least one of a thread or fiber knotted to or threaded through the proximal and distal apices of the zig zag stents.

4. A deployment device and stent assembly as in claim 3 wherein the thread or fiber is knotted alternately to a distal apex of one stent and then a proximal apex of an adjacent stent to provide a link thread of zig zag configuration.

5. A deployment device and stent assembly as in claim 1, wherein the plurality of trigger wires comprises three trigger wires extending from the release mechanism through the lumen.

6. A deployment device and stent assembly as in claim 1 wherein the stent assembly comprises a plurality of self expanding zig zag stents and a link arrangement between adjacent stents so that the stents are linked together to define an elongate substantially cylindrical lumen wall engaging surface, each stent having a plurality of struts and bends between the struts and the link arrangement comprising at least one of a biocompatible thread or fiber such as a suture thread and knots which are knotted alternately to a bend of one stent and then a bend of an adjacent stent to provide a link thread of zig zag configuration, whereby upon endoluminal placement by endovascular deployment, the stent assembly is adapted to provided pressure on the wall of the lumen with each stent able to act independently of an adjacent stent.

7. A method of treatment of a false lumen of an aortic dissection comprising the steps of a) loading a stent assembly onto a deployment device, the stent assembly comprising a plurality of self expanding stents linked together and defining an elongate substantially cylindrical lumen wall engaging surface, the deployment device including a retention arrangement to retain a proximal end of the stent assembly in a retracted state and a trigger wire arrangement to release the retention arrangement to thereby release the proximal end of the stent assembly, a sheath to retain the entire stent assembly in a retracted state and means to withdraw the sheath, wherein each of the self-expanding stents is linked to an adjacent self-expanding stent by a thread or a fiber knotted to apices of each of the self-expanding stents to prevent adjacent stents from sliding relative to one another, b) endovascularly deploying the deployment device with the stent assembly loaded thereon to the site of the false lumen, c) withdrawing the sheath to expose the stent assembly such that it provides pressure against a wall of the lumen, d) releasing the proximal end of the stent assembly by means of releasing the trigger wire arrangement, and e) withdrawing the deployment device, and, wherein the retention arrangement comprises a trigger wire sleeve disposed over the elongate catheter, the trigger wire sleeve having a lumen, a plurality of apertures in a sidewall, and a plurality of trigger wires extending through the lumen and looping out of the apertures to releasably engage the proximal end of the stent assembly.

8. A method as in claim 7 wherein a distal end of the stent assembly is also retained to the deployment device and previous or subsequent to the step of releasing the proximal end of the stent assembly, the distal end is released.

9. A method of treatment of aortic dissection disease comprising a two stage process to close off a rupture associated with an aortic dissection and to apply pressure to a false lumen associated with the aortic dissection, the method comprising the steps of: a) endovascularly deploying a first deployment device with a stent graft retained thereon to a site of the aortic dissection, b) checking by radiographic techniques that the stent graft is positioned over a site of a rupture, c) deploying the stent graft from the first deployment device, d) withdrawing the first deployment device, e) endovascularly deploying a second deployment device with a stent assembly loaded thereon to a site of the false lumen, the stent assembly comprising a plurality of self expanding stents linked together and defining an elongate substantially cylindrical lumen wall engaging surface, the deployment device including a retention arrangement to retain a proximal end of the stent assembly in a retracted state and a trigger wire arrangement to release the retention arrangement to thereby release the proximal end of the stent assembly, a sheath to retain the entire stent assembly in a retracted state and means to withdraw the sheath, f) withdrawing the sheath to expose the stent assembly such that it provides pressure against the wall of the lumen, g) releasing the proximal end of the prosthesis by means of releasing the trigger wire arrangement, h) withdrawing the second deployment device and, wherein the first deployment device comprises a trigger wire sleeve disposed over an elongate catheter, the trigger wire sleeve having a lumen, a proximal end, a plurality of apertures in a sidewall of the proximal end, a plurality of trigger wires extending through the lumen and looping out of the apertures, at least one length of filament joining proximal apices and knotted to the proximal apices to form a length of filament between adjacent apices, wherein the at least one length of filament forms a plurality of engagement loops, each of which engages one of the plurality of trigger wires and pulls the plurality of proximal apices toward the elongate catheter.

10. A method as in claim 9 wherein a distal end of the stent assembly is also retained to the deployment device and previous or subsequent to the step of releasing the proximal end of the prosthesis, the distal end is released.

11. A deployment device and stent assembly in combination, the stent assembly comprising a plurality of self expanding zig zag stents together defining an elongate substantially cylindrical lumen wail engaging surface, links between adjacent stents, the links comprising a suture thread threaded and knotted alternately to a bend of one stent and then a bend of an adjacent stent to connect the stents and to prevent adjacent stents from sliding relative to one another, and a proximal end of the stent assembly comprising a proximal stent having proximal bends, a circumferential biocompatible thread extending through the proximal bends and including thread portions between adjacent bends of the proximal end of the proximal stent;

the deployment device comprising an elongate catheter adapted to be deployed over a guide wire, a nose cone at a proximal end of the elongate catheter, a trigger wire retention arrangement including at least one trigger wire to retain a proximal end of the stent assembly just distal of the nose cone, the trigger wire retention arrangement comprising a trigger wire sleeve disposed over the elongate catheter, the trigger wire sleeve having a lumen, a proximal end, and at least one aperture in a sidewall of the enlarged proximal end, wherein the at least one trigger wire extends through the lumen and loops out of the at least one aperture to engage the proximal end of the stent assembly, a sheath over the elongate catheter adapted to retain the stent assembly in a contracted state around the elongate catheter, and a release arrangement at a distal end of the elongate catheter to release the trigger wire arrangement and a grip mounted to the sheath to enable withdrawal of the sheath.

* * * * *